United States Patent [19]

Bischoff et al.

[11] Patent Number: 4,806,490

[45] Date of Patent: Feb. 21, 1989

[54] PROCEDURE FOR THE DETECTION OF ALLERGEN-CONTAINING HOUSE DUST

[75] Inventors: Edelbert Bischoff, Kirchheim-Bolanden; Wolfgang Schirmacher, Mainz, both of Fed. Rep. of Germany

[73] Assignee: Werner & Mertz GmbH, Mainz, Fed. Rep. of Germany

[21] Appl. No.: 16,623

[22] Filed: Feb. 19, 1987

Related U.S. Application Data

[63] Continuation-in-part of Ser. No. 698,114, Feb. 4, 1985, abandoned, which is a continuation-in-part of Ser. No. 673,948, Nov. 21, 1984, abandoned, and a continuation-in-part of Ser. No. 767,479, Aug. 20, 1985, abandoned.

[30] Foreign Application Priority Data

| Dec. 6, 1983 | [DE] | Fed. Rep. of Germany | 3344087 |
| Feb. 10, 1984 | [DE] | Fed. Rep. of Germany | 3404821 |
| Aug. 22, 1984 | [DE] | Fed. Rep. of Germany | 3430896 |

[51] Int. Cl.$^4$ .......................................... G01N 21/78
[52] U.S. Cl. ........................................ 436/98; 436/8; 436/164; 436/169; 436/178; 436/179; 436/183; 436/513; 436/903
[58] Field of Search ............... 436/8, 91, 96, 98, 110, 436/164, 169, 175, 178, 179, 183, 513, 903

[56] References Cited

U.S. PATENT DOCUMENTS

| 3,585,004 | 6/1971 | Mast .................................. 422/56 |
| 3,684,451 | 8/1972 | Linoli et al. ..................... 436/169 X |
| 3,953,588 | 4/1976 | Nieschulz et al. .............. 436/513 X |
| 3,995,023 | 11/1976 | Nieschulz et al. .............. 436/513 X |
| 4,003,706 | 1/1977 | Szekely .......................... 436/110 |
| 4,027,006 | 5/1977 | Nieschulz et al. .............. 436/513 X |
| 4,031,199 | 6/1977 | Nieschulz et al. .............. 436/513 X |

FOREIGN PATENT DOCUMENTS

| 3344087 | 4/1985 | Fed. Rep. of Germany. |
| 2502786 | 10/1982 | France. |
| 0046518 | 11/1977 | Japan ................................ 436/110 |

OTHER PUBLICATIONS

Bischoff et al, Chemical Abstracts, vol. 102, No. 15, Abstract No. 102:128184e, 4/15/85.

Baldo et al, Naturwissenschaften, vol. 64, No. 11, pp. 594–595, 1977.

Tovey et al, Int. Archs. Allergy Appl. Immun., vol. 75, No. 3, pp. 322–329, Dec. 1984.

Kamel et al, Chemical Abstracts, vol. 93, Abstract No. 93:163803y, 1980.

Bronswijk et al, Allergy and Immunology, vol. 24, pp. 18–28, 1978.

Petri et al, Allergologie, vol. 5, No. 3, pp. 109–119, 1982.

*Luftqualitat in Innenraumen,* Hrgb. K. Aurand, B. Siefert and J. Wegner, Gustav Fischer Vertag, Stuttgart-New York, 1982, pp. 385–401.

Jorde et al, Allergologie, vol. 7, No. 4, pp. 123–126, 1984.

Jorde et al, Allergologie, vol. 6, No. 10, pp. 368–371, 1983.

Shapiro, Progress in Nucleic Acid Research, vol. 8, pp. 73–112, 1968.

Bronswijk, J. Med. Ent., vol. 10, No. 1, pp. 63–70, 1973.
Allergologie, Jahrgang 7, NR. 11/1984, S. 446–449 Bischoff et al.

Allergologie, Jahrgang 8, NR. 1/1985, S.36–38, Bischoff et al.

*Primary Examiner*—Barry S. Richman
*Assistant Examiner*—Robert J. Hill, Jr.
*Attorney, Agent, or Firm*—Ladas & Parry

[57] ABSTRACT

The invention relates to a procedure to establish the presence of allergen-containing housedust, as results when or after housedust mites occur, in which samples of dust present in buildings are thoroughly suspended in a aqueous-alcoholic alkali metal hydroxide solution and, with the resulting extract, a color reaction using an aromatic diazo compound is carried out, the color reaction being evaluated with respect to its occurrence as an indication of the pollution of the dust with housedust mite residues. According to a particular embodiment, a paper treated with the aromatic diazo compound (and where appropriate with starch) is used for carrying out the color reaction. A further aspect of the invention involves quantitatively determining the allergological activity resulting from housedust mites in housedust samples.

23 Claims, No Drawings

PROCEDURE FOR THE DETECTION OF ALLERGEN-CONTAINING HOUSE DUST

The present application is a continuation-in-part of our patent application Ser. No. 698,114 filed Feb. 4, 1985, now abandoned, which itself is a continuation-in-part of Ser. No. 673,948 filed Nov. 21, 1984, now abandoned, as well as a continuation-in-part our patent application Ser. No. 767,479 filed Aug. 20, 1985, now abandoned.

The present invention concerns a process for the detection of allergen-containing housedust and a process for quantitatively determining the allergological activity resulting from housedust mites in a housedust sample.

The occurrence of housedust mites (Dermatophagoides pteronyssinus, farinae etc.) has attracted increasing attention in recent times (see G. Hoffmann in "Luftqualität in Innenräumen" (The quality of indoor air) published by Gustav Fischer, Stuttgart—New York, 1982, pages 385 to 401). The reason for this interest is that it has been established that a considerable fraction of the population—about 5%—suffers from asthmatic symptoms which are attributable to constituents of housedust.

These constituents are principally the feces of the abovementioned housedust mites and fragments of dead mites. The intestinal tract of the live and dead mites contains the allergens which induce the disturbances of health (see Petri et al. in Allergologie, Vol. V, No. 3/1982, pages 109 to 119). A live mite itself contains only about one thousandth of the amount of allergen which it produces in the course of its life. The feces themselves are frequently colonized by fungi which, in turn, may likewise produce allergens. The major amount of allergens is found in dust deposits, even when the original mite population has been killed off or reduced by control measures.

The housedust mites reside in upholstered furniture, beds, floors and walls, especially when they are covered with textile materials. With respect to total area, it is probably carpets which make the greatest contribution.

A very fine dust is raised from floors and upholstered furniture when walked upon and used, and this frequently collects in inaccessible places which are essentially free of air drafts, for example behind cupboards. Even the very process of vacuum cleaning raises some of this very fine dust, and thus it reaches places which are not themselves colonized by mites. In any event, the more dust that is raised, the greater is the annoyance to those in the rooms affected.

Elimination of the causes of housedust allergy presupposes that the cause is known, for there are also other allergies, such as, for example, to pollen (hayfever). However, housedust allergy is a nuisance throughout the year for those affected since mite feces and mite residues are present virtually without interruption. Thus, the physician and patient are repeatedly confronted by the question of whether there is infestation with mites.

On the basis of the present state of the art, the only method of detection is microscopic recognition of the mites themselves. However, this procedure is associated with such great difficulties that it can be carried out in only a few laboratories which specialize in it. This entails the necessity of taking the dust sample, dispatching the same under prescribed conditions, and then investigating it in the laboratory. Since the mites cannot be recognized in the presence of other dirt, it is necessary for them to be removed from the dust sample and then identified.

The most widely used known process of removal comprises flotation, associated with manual isolation of the floating animals and their identification under the microscope (see J. E. M. H. van Bronswijk et al. in Allergie und Immunol. 24 (1978), pages 18 to 28). Aside from the fact that this can be carried out only by experienced experts, it should be emphasized that a considerable amount of time must be expended to process a sample; in addition, there is the dispatch and risk of the sample changing during transport.

All identification procedures which are based on the presence of the mites themselves are associated with the disadvantage that no information about the pollution of the dust with allergens, which are the actual cause of the disorder, can be obtained.

Dust samples, especially those of very fine structure, such as are deposited from the air after having been raised, may be particularly rich in allergens and contain few mites or even none at all.

Thus an object according to the invention is to provide a straightforward and reliable detection procedure for the recognition of allergen-containing housedust.

It has now been established in accordance with one aspect of the present invention that a considerably more straightforward detection, which characterizes the pollution of the housedust with excretion products of the housedust mites, can be managed irrespective of whether live or dead mites are present at the instant of detection or not.

The detection is associated with constituents of the excretion products of the mites as are found in toth the digestive tract of the mites themselves and in their excreta.

This detection can be carried out without problems both by experts and by lay people, and it provides not only information on the presence of excreta of housedust mites in the housedust, but it also permits an assessment of the instantaneous or previous infestation with mites.

The detection procedure according to the invention to establish the presence of allergen-containing housedust, as results when or after housedust mites occur, comprises thoroughly suspending in an aqueous-alcoholic alkali metal hydroxide solution, samples of dust which is present in buildings, and carrying out with the resulting extract a color reaction using an aromatic diazo compound, the color reaction being evaluated with respect to its occurrence as an indication of the pollution of the dust with housedust mite residues.

The following should be specifically noted for carrying out the detection procedure according to the invention so as to determine the presence of the allergen-containing dust essentially on a qualitative basis. The alcohol used for the aqueous-alcoholic solution is preferably an alcohol which is freely miscible with water, such as, for example, lower monohydric aliphatic alcohols. Methanol is particularly preferred for this; however, it is also possible to use ethanol. The weight ratio of alcohol to water in the aqueous-alcoholic solution can vary, and it is generally about 10:90 to about 95:5. A weight ratio of alcohol to water of (50 to 90):(50 to 10), in particular of (75 to 90) : (25 to 10), has proved particularly useful.

The alkali metal hydroxide used in the aqueous-alcoholic solution is preferably potassium hydroxide or sodium hydroxide. However, it is also possible to use lithium hydroxide. The amount of the alkali metal hydroxide in the aqueous-alcoholic solution can vary; it is generally about 0.1 to about 50% by weight. An alkali metal hydroxide content of about 0.1 to about 20% by weight is advantageous, and about 0.1 to about 10% by weight is preferred. In a very particularly preferred manner, the alkali metal hydroxide content in the aqueous-alcoholic solution is about 4 to 5% by weight.

In principle, the compounds suitable for the color reaction are all those which give a color reaction with the dust containing the mite residues. The reaction used in this aspect of the present invention is based on the ability of the mite residues (residues of mite feces and fragments of dead mites) to give a color reaction with aromatic diazo compounds. Thus, a suitable aromatic diazo compound is every aromatic diazo compound which undergoes a color reaction with the extraction solution (in the case of the presence of housedust mite residues). Diazosulfanilic acid (4-diazobenzenesulfonic acid), which gives a brick-red coloration, has proved particularly useful as the aromatic diazo compound. In one embodiment the aromatic diazo compound can be used in the solid form (where appropriate stabilized in a customary manner) or in the form of an aqueous, in particular saturated, solution.

A second embodiment according to this aspect of the invention comprises using a paper which has been heated with the diazo compound and, where appropriate, with starch for carrying out the color reactive between the extract and the aromatic diazo compound.

In the detection procedure according to the present invention, it is advantageous to proceed in such a manner that a dust sample which has been obtained is (after removing the coarse fractions) impregnated with the aqueous-alcoholic alkali metal hydroxide solution. For this, it is possible to vary the volume ratio of the dust sample to the extraction solution. In general, this volume ratio of the dust sample to the extraction solution is about 0.1:1 to about 2:1. A volume ratio of about 0.5:1 has proved particularly useful. It is preferred that the amount of said solution in relation to the amount of the housedust sample extracted be minimized so as to intensify any color intensity resulting from the contacting step.

The extraction solution is added to the dust sample and they are thoroughly mixed by shaking or stirring. The resulting extract suspension is allowed to stand, whereupon the dust generally settles out of the extraction solution (a few minutes).

In the first embodiment of this aspect of the invention an aromatic diazo compound, in particular diazosulfanilic acid (4-diazobenzenesulfonic acid), is added to the dust sample to which the extraction solution has been added. This is carried out by, for example, addition of the aromatic diazo compound in the solid form which is, where appropriate, stabilized. However, in place of this it is also possible to meter in the aromatic diazo compound in the dissolved form, in particular as a saturated aqueous solution (a few drops). The whole is then thoroughly mixed by shaking or stirring. The resulting extract suspension is allowed to stand, whereupon the dust generally settles out of the extract solution (a few minutes).

In the second embodiment of the invention referred to above, the extraction solution is then brought into contact with the paper which has been treated with the aromatic diazo compound (and where appropriate with starch). This is advantageously carried out by immersing the treated paper in the extraction solution.

In either embodiment because of the presence of the aromatic diazo compound, for example diazosulfanilic acid, in the extract solution or on the treated paper, when mite excreta are present a brick-red coloration forms in the solution or on the paper, respectively, and the intensity of this is, as the Applicant has established, proportional to the concentration of mite feces present in the dust sample.

In order to make the color detection clearer in the first embodiment, it is possible to remove the supernatant extraction solution (over the sedimented dust) and to assess the color intensity in this form. However, it is also possible to immerse a small strip of white filter paper of defined size (for example 0.5 cm$^2$) in the color solution and to evaluate the coloration remaining on the paper.

The preferred practice of the second embodiment according to this aspect of the invention takes the form of treating a paper strip, for example filter paper, with the aromatic diazo compound (for example with about 5% by weight of diazo compound relative to the paper) and of immersing the paper strip thus treated directly in the supernatant extraction solution, whereupon the color reaction takes place on the paper. The use is comparable with that of pH indicator paper. Under defined detection conditions, the color developed can be compared with a color scale provided. Then, by means of a comparison of this type with a standardized color scale, conclusions can be drawn about the intensity of housedust mite residues in the housedust.

In the case of the procedure mentioned, that is to say the treatment of a paper strip with the aromatic diazo compound, it has proved to be particularly advantageous to apply the aromatic diazo compound together with starch (amylum) to the paper strip. By this means, it is possible to achieve in the color reaction an even more uniform coloration on the paper strip treated in this manner. The amount of starch used together with the aromatic diazo compound can vary; however, it is generally about 50% by weight of the amount of the aromatic diazo compound. In this connection, the applicant has established, in a surprising manner, that a paper strip treated with the aromatic diazo compound (for example a paper strip treated with about 50 mg of diazosulfanilic acid per g of paper, and with about 25 mg of starch per g of paper) can be stored stable, without hazard and without any risk over a prolonged period (for several months); in view of the known properties of aromatic diazo compounds, this is thoroughly unexpected.

The detection procedure itself is based on some specific findings, which are to some extent surprising:

(1) In order, using the aqueous-alcoholic extraction solution at room temperature, to extract rapidly and exhaustively the feces constituents which are relevant for the color detection, an alkali metal hydroxide solution (for example of KOH or NaOH) in the indicated concentration is necessary (a sodium carbonate solution of corresponding concentration, which would actually be necessary according to number (2) below, is unsuccessful).

(2) The color reaction with the aromatic diazo compound, in particular with diazosulfanilic acid, would per se take place best only in aqueous solution which is alkaline with sodium carbonate. (In only aqueous alkali metal hydroxide solution, for example of KOH or NaOH, the desired color reaction does not take place - as the Applicant has established). However, starting from this particular problem with respect to designing a straightforward detection (qualitative) procedure, it has now been suprisingly found that when an extraction solution of an alkali metal hydroxide in a solvent mixture of alcohol and water, in particular in a mixture in which the weight ratio of alcohol to water is (50 to 90):(50 to 10), is used, the feces constituents relevant for the color detection are extracted virtually quantitatively and the desired color reaction (with the aromatic diazo compound, in particular diazosulfanilic acid) takes place in the same extraction solution. Moreover, the alcohol improves the wetting of the dust samples and, at the same time, brings about a rapid and uniform distribution of color on the detection paper.

Further development of the first aspect of the invention described above has led to a process for quantitatively determining the allergological activity resulting from housedust mites in a housedust sample. Such a process represents a further aspect of the invention. One such process comprises suspending a sample of housedust in an aqueous-alcoholic alkali metal hydroxide solution to form an extract, contacting the extract with an aromatic diazo compound, and quantitatively measuring the intensity of any resulting coloration, the allergological activity of the housedust sample being proportional to the intensity of coloration. A further such process comprises substantially exhaustively extracting the guanine content of the housedust sample and quantitatively determining the allergological activity on the basis of the guanine content in the resulting extract. In particular it has been found that although guanine is not known ordinarily to act as an allergen itself, guanine can be used as an indicator for allergological activity. In fact the actual allergen which is produced by housedust mites is a protein compound of complicated structure.

The improved ability to gain quantitative information on the extent of pollution by allergens resulting from housedust mites contained in such housedust is confirmed by comparison of the results of the measurement in the procedure according to the invention with that test method which, according to the state of the art, is to be regarded as the most effective at present, that is to say, the radioallergosorbent test (RAST).

Statistical analysis of the results of the investigations obtained on the same dust samples both with the RAST and with the procedure described here (using the color reaction), and the relation of them to the mite population checked by microscopy has shown a high degree of agreement in the assessment of the overall allergological activity, the analysis having been carried out by the Spearman correlation coefficient method (Sidney Siegel, "Nonparametric Statistics", McGraw Hill Intern. Book Comp., Auckland (1956)).

Compared with RAST, the procedure according to the invention is more straightforward to carry out, since it is merely necessary to extract the relevant dust sample, and it is then possible directly to measure the color intensity in the extract. Even the design of the RAST method is more elaborate, and its individual steps are subject to the problems appropriate to them; thus, attempts have been made to abandon the use of radioactive substances for indication (in this context, see D. Nolte "Allergiediagnostik" ["The Diagnosis of Allergies"]DustriVerlag, Karl Feistle, Munich-Deisenhofen (1981), in particular pages 29 et seq., and M. Werner and V. Ruppert "Praktische Allergiediagnostik" ["Practical Diagnosis of Allergies"] published by Georg Thieme, Stuttgart (1979), pages 96 et seq.).

These new findings by the applicant on the assessment of the color reaction have led to the further aspect of the invention, namely a quantitative measurement.

Further details for carrying the detection procedure of the first aspect of the invention are indicated below. The found analytic procedure for infestation of housedust with allergen-containing residues from housedust mites is capable of a multiplicity of embodiments. This applies not only to the sampling of the dust, but also to the mixing of the dust with the extraction solution and to the course of the color reaction.

With the aim of particularly efficient collection of dust, a filter (in particular a fabric or paper filter) can be placed in the suction tube of a conventional vacuum cleaner, for example in the form of a small cloth (in particular of a handkerchief). This has the advantage that the fine dust is specifically and concentratedly collected. During the sampling itself, account has to be taken of the fact that floors which are frequently vacuum-cleaned may possibly no longer contain a sufficient amount of dust for the detection. In this case, the vacuum-cleaning is advantageously carried out in less accessible places. The dust collection is carried out particularly advantageously by vacuum cleaning upholstered furniture and beds.

Particularly suitable for the extraction of the dust samples are small, closable glass and plastic containers having a capacity of a few milliliters (for example 1 to 10 milliliters), which are provided with gradations for measuring the volume of the dust sample and the extraction solution. However, in specific cases, it is also possible for the extraction of the dust sample to be carried out on, for example, a watchglass.

A further simplification can be achieved in the second embodiment in accordance with the first aspect of the invention - by thickening the low viscosity and to some extent volatile extraction solution with, for example, a customary thickening agent, in particular cellulose ether. The extraction solution thus thickened is preferably initially introduced into small plastic containers. After the measured dust sample has been stirred in, a pasty mass is obtained. For the color detection, one side of the treated paper (for example filter paper treated with the aromatic diazo compound) is pressed on the pasty sample in the container, whereupon a portion of the moist mass of dust remains adherent to the paper when it is lifted off. The coloration is assessed through the other (unsoiled) side of the paper. In this embodiment of the development according to the invention, there is, in particular, a reduction in evaporation and the risk of splashing.

Some preferred embodiments of the procedure according to the further aspect of the invention are described below:

It is preferable that consituents in the dust sample which interfere with the detection be removed by cleaning before the suspending steps to form the extract, such as by treatment of the dust sample with a heated aqueous-alcoholic solvent mixture. The constituents to be detected are removed from the remaining cleaned dust sample by extraction with an aqueous-alcoholic alkali metal hydroxide solution. The aqueous-alcoholic alkali metal hydroxide solution used as the extraction means is preferably strongly alkaline. For this purpose the aqueous-alcoholic solution contains preferably from 0.1 to 20 weight percent, more preferably from 0.5 to 2 weight percent, of the alkali metal hydroxide. Preferred alkali metal hydroxides are sodium hydroxide and potassium hydroxide. Specifically preferred is the use of sodium hydroxide in an amount of about 0.64 weight percent. The aqueous-alcoholic solution is preferably a lower-aliphatic alcohol (more preferably methanol) which is dissolved in water. The alcohol content in the aqueous-alcoholic solution is preferably from 5 to 50 weight percent, more preferably from 10 to 30 weight percent. Especially preferred is an aqueous-alcoholic solution containing about 17 weight percent of methanol. The ratio of alcoholic solution to the housedust sample is preferably maintained to intensify the color intensity resulting from the contacting as discussed above in connection with the first aspect of the invention.

Using detection papers, it is possible to establish, in a preliminary test on a sample of the resulting extract, the color intensity which is to be expected.

For carrying out the contacting between the extraction solvent and the aromatic diazo compound (in connection with the quantitative method of the present invention) it is preferred to carry out this contacting step in the presence of an alkali metal carbonate. Especially preferred is the use of sodium carbonate. The alkali metal carbonate is used in the form of an aqueous solution which preferably contains from 1 to 22 weight percent and more preferably from 10 to 20 weight percent of alkali metal carbonate. The use of an aqueous solution containing 17 weight percent of sodium carbonate is especially preferred.

The contacting step in the presence of an alkali metal carbonate (as above explained) is preferably carried out with an alkali metal carbonate, preferably sodium carbonate used in an amount in excess of that necessary to improve the intensity of any coloration resulting from said contacting step. Such an excess amount of aqueous alkali metal carbonate solution is used so that the resulting mixture is predominantly alkaline. More specifically, 1 to 10 ml, preferably 1 to 5 ml of the extraction solution (test solution) are being taken, depending on the color intensity which is to be expected, and the test solution is mixed with the threefold amount (by volume) of the sodium carbonate solution. In other words, to 1 to 10 parts (by volume) of the test solution are added 3 to 30 parts (by volume) of the sodium carbonate solution. Preferably one dilutes the extract with water prior to contacting the extract with the aromatic diazo compound.

Depending on the intensity, an aliquot of between 1 and 10 ml of the extract is removed, and sodium carbonate solution, and then a suitable aromatic diazo compound, for example diazosulfanilic acid, are added.

After about 20 minutes for color development, an aqueous-alcoholic solvent mixture is added, and the colored solution thus obtained is measured in a spectrophotometer with a blank sample as reference. The result of measurement is evaluated using a guanine calibration curve. The detail of such a procedure should be evident to one skilled in carrying out such analyses.

The efficiency of the procedure according to the first aspect of the invention is illustrated by the following comparison:

20 dust samples which were from various buildings where housedust allergy was suspected and which had been sent in by physicians were first subjected to a biological assessment using the flotation procedure (according to the state of the art, as described above). This evaluation of the samples showed moderate, weak or no infestation.

Subsequently, evaluations according to the invention were carried out on the same samples, in fact by someone who had no knowledge of the (previous) biological assessment. The color reactions according to the invention showed moderate, weak and no infestation. Complete agreement was found on comparison of these results with the laboratory notebook in which the biological findings had been recorded.

EXAMPLE 1

A standard vacuum cleaner is provided with a new dustbag, and the area of textile to be investigated (for example carpets, upholstered furniture, duvets, mattresses) is thoroughly vacuum-cleaned. After the vacuum cleaning is complete, the entire contents of the dustbag are emptied onto a sheet of paper, and the coarse fractions are removed by gently tapping and by picking off. The fine dust remaining on the paper is used for the color detection.

For the color detection, the fine dust sample is measured (about 2 ml) into a glass or plastic cylinder of capacity about 8 ml (diameter about 1.5 cm). Into this is measured about 4 ml of an aqueous-alcoholic extraction solution in which the weight ratio of methanol to water is 75:25 and in which 5% by weight of KOH are dissolved. To this is added the requisite amount of diazosulfanilic acid (1 microspatula tip; about 20 mg/ml dust) and the closed vessel is shaken for about 10 seconds. The vessel is then opened (evolution of gas). After about 3 minutes, a strip of white filter paper (0.5 cm$^2$) is dipped in the extraction solution which has settled, and the brick-red coloration which occurs when there is mite infestation is assessed (this coloration is not formed in the absence of mite residues).

EXAMPLE 2

The dust sampling is carried out in a similar fashion to Example 1.

The fine dust sample (about 0.5 ml) is measured onto a watchglass of diameter about 6 cm, and 10 drops of extraction solution (methanol/water mixture in the weight ratio 90:10, in which 4% by weight of NaOH are dissolved) and 10 drops of saturated aqueous diazosulfanilic acid solution are added. After briefly mixing, one side of a strip of white filter paper of defined size (0.5 cm$^2$) is pressed against the pasty mass. When there is mite infestation, a brick-red coloration emerges, and this is advantageously assessed via the unsoiled side of the paper.

EXAMPLE 3

The dust sampling is carried out in a similar fashion to Example 1.

For the color detection, the fine dust sample is measured (about 2 ml) into a glass or plastic cylinder of capacity about 8 ml (diameter about 1.5 cm). Into this is measured about 4 ml of an aqueous-methanolic extraction solution in which the weight ratio of methanol to water is 75:25 and in which 5% by weight of KOH are dissolved, and the closed vessel is shaken for about 10 seconds. After about 3 minutes, a test strip of filter paper which has been treated with 50 mg of diazosulfanilic acid and 25 mg of water-soluble starch (per g of paper in each case), is dipped briefly in the extraction solution which has settled from the dust (corresponding to the use of a pH paper). When there is mite infestation a brick-red coloration emerges after about 15 seconds at the most (this coloration is not formed in the absence of mite residues).

EXAMPLE 4

The dust sampling is carried out in a similar fashion to Example 1.

The fine dust sample is measured onto a watchglass of diameter about 6 cm, a suitable amount of extraction solution (methanol/water mixture in the weight ratio 75:25, in which 4% by weight of NaOH are dissolved) is added, and the dust is briefly stirred with the extraction solution. Following this, one side of a paper strip treated with diazosulfanilic acid according to Example 3 is pressed against the pasty mass. When there is mite infestation a brick-red coloration emerges on the unsoiled side of the paper after about 15 seconds at the most.

Examples of carrying out the quantitative detection process of the second aspect of the invention follow.

EXAMPLE 5

1. Amount weighed

Amount weighed: 250 mg of allergen-containing housedust.

2. Cleaning

The dust sample is digested with 5 ml "Solution I", which has previously been heated to 60° C., in a 10 ml capacity centrifuge tube. After centrifugation and decanting off, the process is repeated.

3. Extraction

The precleaned dust sample which is still moist is mixed with 3 ml "Solution II" in a centrifuge tube, and is then centrifuged. Rinsing is carried out with 3 ml "Solution I".

4. Color development

The detection solution thus obtained, including the wash solution, is filtered and made up to 100 ml with distilled water in a graduated flask. 1 to 10 ml of this solution (depending on the color intensity which is to be expected on the basis of the preliminary test) is pipetted into a 25 ml graduated flask, 3 ml of 20% strength sodium carbonate solution and 2 ml of 0.05% strength diazosulfanilic acid solution are added. After 20 minutes, 10 ml of "Solution I" are added, and the mixture is then made up to the mark with distilled water.

5. Color measurement

The measurement is carried out at 490 nanometers with a blank sample as reference. Evaluation is carried out using a calibration curve with guanine. (For this purpose, various solutions of guanine (in "Solution II"), containing between 20µg and 100 µg, are prepared in several 25 ml graduated flasks. The color development is carried out in accordance with the method indicated in section 4 for the dust sample).

Solution I: 20 parts by volume of methanol and 100 parts by volume of water;

Solution II: 1.9 g of KOH in 200 ml of "Solution I".

We claim:

1. A process for establishing whether a sample of housedust contains allergens resulting from an occurrence of housedust mites which comprises suspending a sample of housedust from a building in an aqueous-alcoholic alkali metal hydroxide solution to form an extract, contacting the extract with an aromatic diazo compound, and detecting any housedust mite residues in the housedust sample as an indication of whether the housedust sample contains allergens by observing any color change in the extract subsequent to the contacting step, wherein the alkali metal hydroxide content in the aqueous-alcoholic alkali metal hydroxide solution is about 0.1 to about 50% by weight.

2. The process according to claim 1, wherein any color change in the extract subsequent to the contacting step is compared, with respect to intensity of coloration, with a standarized color scale to provide an indication of the concentration of housedust mite residues in the housedust sample.

3. The process according to claim 1, wherein the weight ratio of alcohol to water in the aqueous-alcoholic alkali metal hydroxide solution is from about 10:90 to about 95:5.

4. The process according to claim 1, wherein the volume ratio of the dust sample to the aqueous-alcoholic alkali metal hydroxide solution is from about 0.1:1 to about 2:1.

5. The process according to claim 1, wherein the aromatic diazo compound is such that it produces a dyestuff which is soluble in the aqueous-alcoholic alkali metal hydroxide solution when the housedust sample contains housedust mite residues.

6. The process according to claim 1, wherein the aromatic diazo compound is added to the extract.

7. The process according to claim 1, wherein the aromatic diazo compound is diazosulfanilic acid.

8. The process according to claim 1, wherein the aromatic diazo compound is contained in a paper.

9. The process according to claim 8, wherein the paper also contains starch.

10. The process according to claim 8, wherein the aqueous-alcoholic alkali metal solution incudes a thickening agent.

11. The process according to claim 8, wherein any color change in the extract subsequent to the contacting step is compared, with respect to intensity of coloration, with a standarized color scale to provide an indication of the concentration of housedust mite residues in the housedust sample.

12. The process according to claim 8, wherein the weight ratio of alcohol to water in the aqueous-alcoholic alkali metal hydroxide solution is from about 10:90 to about 95:5.

13. The process according to claim 8, wherein the volue ratio of the dust sample to the aqueous-alcoholic alkali metal hydroxide solution is from about 0.1:1 to about 2:1.

14. A process for quantitatively determining the allergological activity, resulting from household mites, in a housedust sample, wherein the allergological activity depends on the amount of housedust mites and/or mite residues in such a housedust sample, which comprises:
suspending a sample of housedust in an aqueous-alcoholic alkali metal hydroxide solution containing from 0.1 to 20 weight percent alkali metal hydroxide to form an extract,
contacting the extract with an aromatic diazo compound and
quantitatively measuring the intensity of coloration in the extract subsequent to the contacting step, the allergological activity of the housedust sample being proportional to the measured intensity of the coloration.

15. The process according to claim 14, wherein the intensity of coloration measurement is carried out using a spectrophotometer.

16. The process according to claim 14, further including cleaning the housedust sample with an aqueous-alcoholic mixture before the suspending step.

17. The process according to claim 14, further comprising diluting the extract with water prior to contacting the extract with the aromatic diazo compound.

18. A process according to claim 14, wherein the measured intensity of coloration is compared with the intensity of coloration produced by a calibration based on different guanine concentrations.

19. The process according to claim 14, wherein the intensity of coloration in the extract subsequent to the contacting step is compared to a calibration curve which has been obtained by dissolving a series of varying amounts of guanine in an amount of said aqueous-alcoholic alkali metal hydroxide solution to form a series of respective extract solutions and contacting each respective extract solution thus produced with a standard amount of said aromatic diazo compound to provide respective calibration solutions corresponding to this series of guanine amount, said calibration solutions being used to provide respective portions of the calibration curve.

20. The process according to claim 14, wherein the aromatic diazo compound is diazosulfanilic acid.

21. The process according to claim 14, wherein the contacting step is carried out in the presence of sodium carbonate, said sodium carbonate being used in an amount in excess of that necessary to improve the intensity of any coloration resulting from said contacting step.

22. The process according to claim 21, wherein the intensity of coloration measurement is carried out using a spectrophotometer.

23. In a method of quantitatively determining the allergological activity, resulting from household mites, in a housedust sample, wherein the allergological activity depends on the amount of housedust mites and/or mite residues in such a housedust sample, which comprises substantially exhaustively extracting any guanine in a housedust sample from the housedust sample into an extract using an aqueous-alcoholic alkali metal hydroxide solution containing from 0.1 to 20 weight percent of alkali metal hydroxide and quantitatively determining the allergological activity of the housedust sample on the basis of the guanine content in the extract.

* * * * *